(12) United States Patent
Voziyan et al.

(10) Patent No.: US 6,521,645 B2
(45) Date of Patent: Feb. 18, 2003

(54) METHODS FOR THE TREATMENT AND PREVENTION OF URINARY STONE DISEASE

(75) Inventors: Paul Voziyan, Overland Park, KS (US); Billy Hudson, Lenexa, KS (US); Jon Scheimman, Kansas City, KS (US)

(73) Assignee: The University of Kansas Medical Center, Kansas City, KS (US)

( * ) Notice: Subject to any disclaimer, the term of this patent is extended or adjusted under 35 U.S.C. 154(b) by 68 days.

(21) Appl. No.: 09/992,973

(22) Filed: Nov. 14, 2001

(65) Prior Publication Data

US 2002/0115694 A1 Aug. 22, 2002

Related U.S. Application Data

(60) Provisional application No. 60/249,991, filed on Nov. 20, 2000.

(51) Int. Cl.$^7$ ............................................... A61K 31/44
(52) U.S. Cl. ........................... 514/351; 514/8; 514/367; 514/262
(58) Field of Search ........................... 514/351, 8, 369, 514/262

(56) References Cited

U.S. PATENT DOCUMENTS

| | | | |
|---|---|---|---|
| 4,758,583 | A | 7/1988 | Cerami et al. |
| 5,238,963 | A | 8/1993 | Ceramie et al. |
| 5,254,572 | A | 10/1993 | Serfontein |
| 5,288,716 | A | 2/1994 | Speck |
| 5,631,271 | A | 5/1997 | Serfontein |
| 6,043,259 | A | 3/2000 | Dhalla et al. |
| 6,051,587 | A | 4/2000 | Dakashinamurti et al. |

FOREIGN PATENT DOCUMENTS

| | | |
|---|---|---|
| WO | 97/09981 | 4/1997 |
| WO | 99/25690 | 5/1999 |
| WO | 00/21516 | 4/2000 |
| WO | 00/22094 | 4/2000 |
| WO | 00/23063 | 4/2000 |
| WO | 00/59493 | 10/2000 |

OTHER PUBLICATIONS

Alderson et al., (2001) *The American Diabetes Association of 61st Scientific Sessions*, p. 696.
Baker et al., (1998) *J. Urol.* 2177–2181.
Baynes et al., (1998) *J. American Society of Nephrology*, vol. 9: Abstract p628A.
Baynes et al., (1989) in *The Maillard Reaction in Aging, Diabetes, and Nutrition*, ed., Monnier & Bayners, (Alan R. Liss, New York) pp. 43–67.
Borghi et al., (1990) *Brit. J. Urol* 65: 231–235.
Borghi et al., (1999) *Kidney Int.* 55: 2397–2406.
Conyers, et al., (1985) *Aust. N.Z.J. Med.* 15: 353–355.
Curhan et al., (1996) *J. Urol.* 155: 1847–1851.
Curhan et al., (1999) *J. Am. Soc. Nephrol*, 10: 840–845.
Edwards et al., (1990) *Urol. Res*, 18: 393–396.
Holmes et al., (1997) *J. Urol.* 158: 34–37.
Holmes et al., (1998) *J. Urol.* 160: 1617–1624.
Holmes et al., (2000) *Kidney Int.* 57: 1662–1667.
Keung et al., (1995) *Proc. Natl. Acad. Sci.* U.S.A. 92: 8990–8993.
Khalifah et al., (1996) *Biochemistry* 35(15): 4645–4654.
Khalifah, et al., (1997), *J. of the American Society of Nephrology*, 8: pp. A2989.
Khalifah, et al., (1999) *Biochemical and Biophysical Research Communications* 257(2): 251–258.
Khan, S.R. (1997) *World J. Urol.* 15: 236–243.
Laker et al., (1980) *Clin Chem.* 26: 827–830.
Lee et al., (1994) *J. Urol.* 152: 1386–1388.
Mazzachi et al., (1984) *Clin. Chem.* 30: 1339–1343.
Meron et al., (1992) *J. Clin. Endocrin, Metab.* 74: 703–707.
Potenzy et al., (1983) *Clin. Chem.* 29: 16–20.
Robertson, W.G., *Urinary tract calculi. In: Metabolic bone and stone disease*.B.E.C. Nordin, ed. Hong Kong, Churchill Livingston, pp. 271–326, 1984.
Rooney et al., (1983) *J. Med. Chem.* 26: 700–714.
Scheinman, (1991) *Kidney Int.* 40: 389–399.
Solomons et al., (1967) *N. Engl. J. Med.* 276: 207–210.
Sun et al., (1996) *J. Urol.* 156: 903–905.
Thorpe & Baynes, (1996) *Drugs & Aging*, vol. 9: No. 2, pp. 69–77.
Tu et al., (1995) *J. Biol. Chem.* 270: 28402–28407.
Tully et al., (1984) *FASEB J.* 8: 343–349.
Uribarri et al., (1989) *Ann. Int. Med.* 111: 1066–1009.

*Primary Examiner*—Rebecca Cook

(57) ABSTRACT

The present invention provides methods and pharmaceutical compositions for treating or inhibiting urinary stone disease that involve administering to an individual with urinary stone disease or at risk of developing urinary stone disease an amount effective of pyridoxamine to reduce urinary oxalate concentrations.

22 Claims, No Drawings

METHODS FOR THE TREATMENT AND PREVENTION OF URINARY STONE DISEASE

CROSS REFERENCE

This application claims priority from U.S. Provisional Patent Application Serial No. 60/249,991 filed Nov. 20, 2000.

STATEMENT OF GOVERNMENT SUPPORT

This research has been supported by the Research grant DK-18381-28 from National Institute of Diabetes, Digestive and Kidney Disease.

BACKGROUND OF THE INVENTION

Urinary stone disease, urolithiasis, affects about 2 to 3% of the general population in the United States and other industrialized countries (1). In some population groups the occurrence can be significantly higher. For example, the prevalence of urolithiasis among adults in Taiwan reaches 8 to 9%, and urinary stones were reported to be the third most common disease in northern Italy (2,3). The incidence of urinary stones further increases with age, in part, due to age-related conditions such as arterial hypertension (4). The likelihood that a Caucasian male will develop stone disease by age 70 is about 1 in 8 (1). While extracorporeal shock wave lithotripsy has-simplified urinary stone removal, the recurrence rates remain high, reaching 50% to 70% in 10 years (5,6).

Since a majority of urinary stones (75–80%) are made of calcium oxalate, the control of concentrations of calcium and/or oxalate in urine is an important part of a medical treatment program to prevent stone formation or recurrence. Hypercalciuria is more common in patients with recurrent calcium oxalate renal stones; it is found in 50% of the cases, compared to about 35% for mild hyperoxaluria (1). However, the lowering of urinary oxalate level has a number of advantages. The contribution of oxalate to calcium oxalate saturation is considerably greater than that of calcium. As a result, a relatively small decrease in oxalate concentration could lower the calcium oxalate level below saturation, and thus prevent stone formation. In addition, changing the calcium concentration in urine is difficult, and risks increased oxalate absorption; it may also affect important physiological processes, such as bone calcification.

Control of urinary oxalate through the diet can produce only a partial effect, because dietary oxalate contribution to urinary oxalate is only 8 to 40% (1,7), with the rest of it synthesized endogenously, mainly in liver. The key reactions of oxalate synthesis are the conversion of glycolaldehyde to glycolate by aldehyde dehydrogenase, the conversion of glycolate to glyoxylate by glycolate oxidase and the oxidation of glyoxylate to oxalate by lactate dehydrogenase. Several minor reactions such as catabolism of hydroxyproline and degradation of aromatic amino acids may also contribute to glyoxylate and oxalate synthesis. However, in vivo, the combined contribution from these reactions is probably less than 5% (8). Glyoxylate can be converted back to glycolate by the action of D-glycerate dehydrogenase (8).

The most extreme example of a disease in which an increase in metabolically derived oxalate leads to urinary stone formation is the clinical syndrome of primary hyperoxaluria. Type I primary hyperoxaluria is characterized by a genetic defect in the peroxisomal vitamin $B_6$-dependent enzyme alanine:glyoxylate aminotransferase (AGT). This defect results in decreased conversion of glyoxylate to glycine; consequently, conversion of glyoxylate to oxalate increases. Type II primary hyperoxaluria is caused by the deficiency of D-glycerate dehydrogenase (8). Patients with these disorders have severe renal stone disease leading to renal failure, and will eventually require renal and hepatic transplantation. Lowering urinary oxalate in these patients can alleviate the severity of stone disease and avoid costly transplantation procedures.

Acquired hyperoxaluria may be caused by a number of factors, such as the gluttony for oxalate-rich foods, abuse of ascorbic acid (vitamin C), and by small bowel disease or bypass of the small intestine that causes increased colonic oxalate absorption. In these cases, lowering urinary oxalate concentration can significantly diminish the probability of stone formation.

About 25% of all stone formers have no quantifiable abnormalities of urinary composition. This condition, called idiopathic stone disease, is likely caused by low activity of normal urinary inhibitors of crystal nucleation and crystal growth. Even though urinary oxalate in these individuals is within a normal concentration range, lowering it will decrease the contribution of oxalate to calcium oxalate supersaturation, and thus lower the probability of stone formation.

Development of an effective drug therapy that decreases urinary oxalate concentration can be a valuable tool in the prophylaxis and treatment of urinary stone disease. Several pharmacological approaches have been tested in an attempt to develop such therapy. One approach is to inhibit the enzymes involved in oxalate biosynthesis. Several inhibitors of either aldehyde dehydrogenase or glycolate oxidase were tested in both animals and humans with mixed results (9,10). Newer inhibitors of aldehyde dehydrogenase may also be used (11,12). However, one drawback of this approach may be the accumulation of glycolaldehyde, a potentially toxic agent.

Another approach to reduction of urinary oxalate concentration is based on the use of the vitamin $B_6$ precursor pyridoxine. This treatment benefits only a small number of patients with vitamin $B_6$-dependent type I primary hyperoxaluria (13). The mechanism of this effect is not clear, but may be related to the ability of pyridoxal-5'-phosphate to modulate protein expression, in particular, the expression of AGT (14). The reports on the effects of pyridoxine in individuals without Type I primary hyperoxaluria are controversial. The intake of pyridoxine in doses of 40 mg/day is associated with reduced risk of kidney stone formation in women (15) but not in men (16). On the other hand, prescription of 200 mg of pyridoxine daily did not reduce urinary oxalate levels in stone formers (17). If the primary mode of pyridoxine action is the regulation of AGT expression and/or activity, these controversial results may reflect individual differences in enzyme status and, thus, may render many stone formers non-responsive to pyridoxine treatment.

The most recent development in the field has been with an approach to trap glyoxylate in liver and reduce the amount available for conversion to oxalate. It is suggested that this approach has a significant potential because of the proximity of glyoxylate to the terminal step in oxalate synthesis. One of the proposed treatments relies on the reactivity of the glyoxylate carbonyl group with the free sulphydryl group of cysteine. The cysteine precursor, (L)-2-oxothiazolidine-4-carboxylate (OTZ) is used as the therapeutic agent because of its low toxicity. OTZ has been shown to decrease urinary oxalate concentration in a rat model of hyperoxaluria (18). Treatment with OTZ also resulted in decreased urinary oxalate levels in normal individuals (19). However, at elevated levels, free cysteine can interfere with a variety of reduction-oxidation reactions in the cell, and is potentially cytotoxic. In a human study, OTZ administered to patients for only 48 hours, produced a number of the mild to moderate adverse effects (19).

Based on all of the above, there is a need in the art for effective methods to treat and prevent urinary stone disease.

SUMMARY OF THE INVENTION

The present invention provides methods and pharmaceutical compositions for treating or inhibiting urinary stone disease that comprise administering to an individual with urinary stone disease or at risk of developing urinary stone disease an amount effective of pyridoxamine to reduce urinary oxalate concentrations. In one set of embodiments, the methods comprise treating an individual suffering from urinary oxalate stones. In another set of embodiments, the methods comprise treating an individual at risk for urinary stone disease in order to reduce or prevent formation of urinary stones in the individual.

DETAILED DESCRIPTION OF THE INVENTION

In one aspect, the present invention provides methods for treating an individual with urinary stone disease with an amount effective of pyridoxamine to reduce urinary oxalate concentrations. As used herein, the term "urinary stone disease" (urolithiasis) means a condition characterized by stone formation in the urine. Conditions leading to urinary stone disease include, but are not limited to the elevated excretion of urinary oxalate (hyperoxaluria), elevated excretion of urinary calcium (hypercalciuria), low excretion of urinary citrate (hypocitraturia), and low activity of the inhibitors of calcium oxalate crystal nucleation and growth.

As used herein, the term "urinary oxalate" means oxalic acid in an individual's urine.

In a preferred embodiment of this aspect of the invention, the urinary stone disease comprises the production of calcium oxalate urinary stones. In a further embodiment, the individual has hyperoxaluria, an elevated urinary oxalate excretion. As used herein, the term "elevated urinary oxalate excretion" means urinary oxalate excretion exceeding 45 mg per day per individual. Normal levels of oxalate a considered to be 8–45 mg/day, so levels that exceed 45 mg/day constitute hyperoxaluria. These levels can reach 90 to 270 mg/day in patients with primary hyperoxaluria.

In another example, the hyperoxaluria comprises primary hyperoxaluria. As used herein, the term "primary hyperoxaluria" means a genetic defect predisposing an individual to hyperoxaluria, including but not limited to Type I and Type II primary hyperoxaluria.

As used herein, "Type I hyperoxaluria" means a genetic defect in the peroxisomal vitamin $B_6$-dependent enzyme alanine:glyoxylate aminotransferase (AGT). This defect results in decreased conversion of glyoxylate to glycine; consequently, conversion of glyoxylate to oxalate increases.

As used herein, "Type II hyperoxaluria" means a genetic deficiency of D-glycerate dehydrogenase.

In a further embodiment, the hyperoxaluria comprises acquired hyperoxaluria. As used herein "acquired hyperoxaluria" means hyperoxaluria that is not due to a genetic inheritance of the disease, and includes hyperoxaluria due to the gluttony for oxalate-rich foods, abuse of ascorbic acid (vitamin C), or due to small bowel disease or bypass of the small intestine that causes increased colonic oxalate absorption.

In another embodiment, the individual has hypercalciuria, an elevated excretion of urinary calcium. As used herein, "elevated excretion of urinary calcium" means excretion of more than 300 mg calcium/day/individual or greater than 4 mg calcium/kg body weight/day. Major causes of hypercalciuria include vitamin D-dependent increase in intestinal calcium absorption associated with primary hyperparathyroidism, i.e. excessive production of parathyroid hormone (serum hormone concentration is >65 pg/ml), and low calcium re-absorption by the kidney.

In another embodiment, the individual has hypocitraturia, low excretion of urinary citrate. Urinary citrate forms a soluble salt with calcium, thus reducing the amount of free calcium available to form calcium oxalate. As used herein, the term "low excretion of urinary citrate" means excretion of less than 200 mg of citrate/day/individual.

In another embodiment, the individual has idiopathic stone disease caused by low activity of the inhibitors of calcium oxalate crystal nucleation and growth. Such inhibitors include, but are not limited to the glycoproteins nephrocalcin and osteopontin, which interact with crystals and inhibit their growth. Their low activity is presumably due to genetically-based abnormalities in protein structure. An average level of nephrocalcin in the urine is 15 mg/dl.

Pyridoxamine can be administered as the sole active pharmaceutical agent, or it can be used in combination with one or more other agents useful for treating urinary stone disease, including but not limited to (L)-2-oxothiazolidine-4-carboxylate (OTZ), allopurinol, inhibitors of aldehyde dehydrogenase, inhibitors of glycolate oxidase, nephrocalcin and osteopontin; or in combination with therapies such as extracorporeal shock wave lithotripsy and reduced oxalate level diets. As used herein, the term "reduced oxalate level diet" means diet from which oxalate-rich foods (rhubarb, spinach and other leafy vegetables, cashews, almonds, and strong tea) have been eliminated.

As used herein, the term "extracorporeal shock wave lithotripsy" means the in situ fragmentation of stones in the kidney, renal pelvis, or ureter by exposing them to ultrasonic waves.

When administered as a combination, the therapeutic agents can be formulated as separate compositions that are given at the same time or different times, or the therapeutic agents can be given as a single composition.

In another aspect, the present invention provides methods for preventing urinary stone disease in an individual at risk of developing urinary stone disease, by administering to the individual an amount effective of pyridoxamine to reduce urinary oxalate concentrations. As used herein, an individual is "at risk of developing a urinary stone disease" if one or more of the following conditions apply: they have previously had urinary stone disease; they have an elevated urinary oxalate excretion, as defined above; they have a genetic predisposition to primary hyperoxaluremia as defined above; they have elevated excretion of urinary calcium (hypercalciuria) as defined above, they have lowered excretion of urinary citrate (hypocitraturia) as defined above, or they have low levels of the inhibitors of calcium oxalate crystal nucleation and growth, as defined above.

In various preferred embodiments of this aspect of the invention, the individual is further treated with one or more compounds selected from the group consisting of (L)-2- oxothiazolidine-4-carboxylate (OTZ), allopurinol, inhibitors of aldehyde dehydrogenase, inhibitors of glycolate oxidase, nephrocalcin and osteopontin; and/or with a reduced oxalate level diet.

The pyridoxamine may be made up in a solid form (including granules, powders or suppositories) or in a liquid form (e.g., solutions, suspensions, or emulsions). Pyridoxamine may be applied in a variety of solutions and may be subjected to conventional pharmaceutical operations such as sterilization and/or may contain conventional adjuvants, such as preservatives, stabilizers, wetting agents, emulsifiers, buffers etc.

For administration, the pyridoxamine is ordinarily combined with one or more adjuvants appropriate for the indicated route of administration. Pyridoxamine may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the pyridoxamine may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials known in the art.

Pharmaceutical compositions containing pyridoxamine are administered to an individual in need thereof. In therapeutic applications, for example, pyridoxamine is administered to an individual suffering from urinary stone disease in an amount sufficient to reduce urinary oxalate concentrations, and to thereby reduce or eliminate the occurrence of calcium oxalate urinary stones. Amounts effective for this use depend on factors including, but not limited to, the route of administration, the stage and severity of the urinary stone disease, the general state of health of the individual, and the judgment of the prescribing physician. Pyridoxamine is safe and effective over a wide dosage range. However, it will be understood that the amount of pyridoxamine actually administered will be determined by a physician, in the light of the above relevant circumstances.

Pyridoxamine may be administered by any suitable route, including orally, parentally, by inhalation or rectally in dosage unit formulations containing conventional pharmaceutically acceptable carriers, adjuvants, and vehicles, including liposomes. The term parenteral as used herein includes, subcutaneous, intravenous, intraarterial, intramuscular, intrasternal, intratendinous, intraspinal, intracranial, intrathoracic, infusion techniques, intracavity, or intraperitoneally. In a preferred embodiment, pyridoxamine is administered orally.

EXAMPLES

Determination and Characterization of Pyridoxamine-glycolaldehyde and Pyridoxamine-glyoxylic Acid Adducts Pyridoxamine dihydrochloride, glycolaldehyde (GLA), glyoxylate (GA), and 2,4-dinitro-phenylhydrasine (DNPH) were purchased from Sigma (St. Louis, Mo.). Samples containing 10 mM GLA or 10 mM GA dissolved in 200 mM Na-phosphate buffer, pH 7.5 were incubated either alone or with 15 mM pyridoxamine for up to 180 min. The carbonyl groups of GLA or GO were determined using DNPH method. 20 $\mu$l aliquots of the samples were mixed with 1 ml of 200 $\mu$M DNPH in 1 M HCI. After 20 minutes at room temperature, the amount of reacted carbonyls was determined by measuring absorbance at 380 nm. The measurements obtained from the samples that did not contain pyridoxamine were used as reference values to calculate fraction of free carbonyl groups in pyridoxamine-treated samples. The above samples were also analyzed in positive ion mode using electrospray ionization mass spectrometry.

Because of its amino group, pyridoxamine can potentially react with carbonyl compounds. In our experiments, pyridoxamine reacted with both oxalate precursors, glycolaldehyde and glyoxylate. The reactivity of pyridoxamine with glycolaldehyde was about 5-fold greater than its reactivity with glyoxylate, but over 75% of either compound was trapped by pyridoxamine after 3 days of incubation at physiological pH and temperature. When reaction mixtures were analyzed using mass-spectrometry, specific reaction products of pyridoxamine and glyoxylate (m/z=318) or pyridoxamine and glycolaldehyde (m/z=193 and m/z=385) were detected. These data indicate that pyridoxamine can trap carbonyl intermediates of oxalate biosynthesis with formation of specific pyridoxamine-carbonyl adducts that are detectable by mass-spectroscopy.

Treatment of Rats With Pyridoxamine

Two month old Sprague-Dawley rats were housed individually in metabolic cages and fed standard powdered stock rations. For 5 more uniform pyridoxamine administration and urine collection, water supply to all animals was limited to 45 ml/day, an average daily water consumption by laboratory rats. Rats in pyridoxamine-treated groups (1.2 $\mu$m/day/gram body weight) were given pyridoxamine in drinking water. The dose of pyridoxamine in these experiments was chosen, based on results from a 7-month pyridoxamine study in a diabetic rat model, where this dose was safe and had therapeutic effects (20). To minimize possible chemical degradation of pyridoxamine, fresh solutions were prepared daily and administered in water bottles wrapped in aluminum foil.

Collection and Analysis of Urine Samples

Twenty-four hour urine samples were collected under toluene (to inhibit bacterial growth) using containers with 2 M hydrochloric acid to minimize spontaneous breakdown of urinary ascorbic acid to oxalate (21). The urine samples were stored at −70° C. until further analysis. Under these conditions, frozen urine can be stored for at least 1 month with no effect on oxalate measurements (22). Collected urine samples were analyzed to determine concentrations of oxalate using the oxalate oxidase method (23). This assay is highly specific and sensitive to about 10 $\mu$M (23). Oxalate oxidase from Barley seedlings was purchased from Sigma Co. (St. Louis, Mo.). The method is based on the conversion of oxalate to hydrogen peroxide and carbon dioxide by oxalate oxidase. The latter was determined enzymatically with horseradish peroxidase by oxidative coupling of 3-methyl-2-benzothiazolinone hydrazone with N,N-dimethylaniline. The resulting colored product was determined spectrophotometrically at 595 nm. The modified sample preparation procedure was used, which replaces column chromatography with a simple precipitation step (24).

Statistical Analysis of the Data

The significance of pyridoxamine effects was determined based on Student-Newman-Kreuls multiple comparison test using Sigma Stat 2.0 program.

Based on the above in vitro data, we predicted that pyridoxamine will trap carbonyl intermediates of oxalate biosynthesis, glycolaldehyde and glyoxylate in vivo. Consistent with this suggestion were the results of our animal experiments. In control animals, daily oxalate excretion increased during the first 5 days (adaptation period) and then remained relatively stable for the course of experiment. In pyridoxamine-treated rats, urinary oxalate levels were consistently lower and became statistically different from controls after 12 days. The water consumption by pyridoxamine-treated animals was similar to that of control animals (i.e., with few occasional exceptions, all 45 ml of daily water allowance were consumed). There was no difference between the groups in either general behavior or in weight gain (Table 1).

Because significant amounts of free pyridoxamine could be present in the urine of pyridoxamine-treated animals, we determined whether pyridoxamine interferes with urinary oxalate determination by oxalate oxidase method. Pyridoxamine added to assay mixtures to a final concentration of 2 mg/ml had no effect on oxalate measurements (data not shown).

TABLE 1

Weight in grams of control and pyridoxamine-treated rats.

|  | Day 1 | Day 26 |
| --- | --- | --- |
| Control | 328 ± 11 | 369 ± 13 |
| Pyridoxamine-treated | 315 ± 6 | 363 ± 16 |

Taken together, these results demonstrate that pyridoxamine treatment can lower urinary oxalate levels in animals. Because the likelihood of calcium oxalate crystal formation increases exponentially with increasing urinary oxalate levels (25), such a reduction in urinary oxalate levels after pyridoxamine treatment would markedly reduce the probability of stone development.

In Vivo Models of Hyperoxaluria

While rats do not spontaneously develop stones (26), hyperoxaluria can be induced in rats, and, like in humans, their oxalate synthesis occurs primarily via the glyoxylate pathway. To determine the effect of pyridoxamine on hyperoxaluria in vivo, two well-established rat models of experimental hyperoxaluria, the ethylene glycol (EG) model and the glycolate model (26) are employed. Both compounds are precursors of oxalate synthesis and their administration results in increased urinary oxalate concentration. The use of the glycolate model allows the bypass of metabolic steps involved in glycolaldehyde biosynthesis and, therefore, demonstrates which oxalate precursor (glycolaldehyde or glyoxylate) is a primary target of pyridoxamine. The use of two different models also helps to minimize possible model-specific adverse effects.

The primary outcome measure is urinary oxalate excretion at the point where pyridoxamine has its maximum predicted effect. Animals are randomized on Day 1 to receive either EG (0.75% solution, in drinking water) or no treatment (Control). The results for Day-14 oxalate are known by Day 15, at which time the animals within each group (Control, EG) are pair-matched according to their Day-14 oxalate. The pyridoxamine and no-pyridoxamine groups therefore begin the pyridoxamine-treatment period with nearly identical mean and standard deviation oxalate excretion, which optimizes the sensitivity of this experimental design. Administration of pyridoxamine is predicted to significantly reduce oxalate excretion, based on the above data.

LITERATURE CITED

1. Menon, M. and Koul, H. (1992) *J. Clin. Endocrin. Metab.* 74, 703–707.
2. Borghi, L., Ferretti, P. P., Elia, G. F., Amato, F., Melloni, E., Trapassi, M. R., and Novarini, A. (1990) *Brit. J. Urol.* 65, 231.
3. Lee, Y. H., Huang, W. C., Chang, L. S., Chen, M. T., Yang, Y. F., Huang, J. K. (1994) *J. Urol.* 152, 1386–1388.
4. Borghi, L., Meschi, T., Guerra, A., Briganti, A., Schianchi, T., Allegri, F., Novarini, A. (1999) *Kidney Int.* 55, 2397–2406.
5. Uribarri, J., Oh, M. S. Carroll, H. J. (1989) *Ann. Int. Med.* 111, 1006–1009.
6. Sun, B. Y., Lee, Y. H., Jiaan, B. P., Chen, K. K., Chang, L. S., Chen, K. T.(1996) *J. Urol.* 156, 903–905.
7. Holmes, R. P. and Kennedy, M. (2000) *Kidney Int.* 57, 1662–1667.
8. Holmes, R. P., Assimos, D. G. (1998). *J. Urol.* 160, 1617–1624.
9. Solomons, C. C., Goodman, S. I., and Riley, C. M. (1967) *N. Engl. J. Med.* 276, 207–210.
10. Rooney, C. S., Randall, W. C., Streeter, K. B., Ziegler, C., Cragoe, E. J., Jr., Schwam, H., Michelson, S. R., Williams, H. W., Eichler, E., Duggan, D. E., Ulm, E. H., Noll, R. M. (1983) *J.Med.Chem.* 26, 700–714.
11. Keung, W. M., Lazo, O., Kunze, L., Vallee, B. L. (1995) *Proc.Natl.Acad.Sci. U.S.A.* 92, 8990–8993.
12. Tu, G. C., Cao, Q. N., Israel, Y. (1995) *J.Biol.Chem.* 270, 28402–28407.
13. Scheinman, J. I. *Kidney Int.* 40, 389–399.
14. Tully, D. B., Allgood, V. E., Cidlowski, J. A. (1994) *FASEB J.* 8, 343–349.
15. Curhan, G. C., Willett, W. C., Speizer, F. E., Stampfer, M. J. (1999) *J.Am.Soc. Nephrol.* 10, 840–845.
16. Curhan, G. C., Willett, W. C., Rimm, E. B., Stampfer, M. J. (1996) *J.Urol.* 155, 1847–1851.
17. Edwards, P., Nemat, S., Rose, G. A. (1990) *Urol.Res.* 18, 393–396.
18. Baker, P. W., Rofe, A. M., Bais, R. (1998) *J.Urol.* 159, 2177–2181.
19. Holmes, R. P., Assimos, D. G., Leaf, C. D., Whalen, J. J. (1997) *J. Urol.* 158,34–37.
20. Alderson, N. L., Metz, T. O., Chachich, M. E., Baynes, J. W., and Thorpe, S. R. (2001) 2001 *The American Diabetes Association 61$^{st}$ Scientific Sessions, p.*696.
21. Conyers, R. A., Bais, R., Rofe, A. M., Potezny, N., Thomas, D. W. (1985) *Aust.N.Z.J.Med.* 15, 353–355.
22. Mazzachi, B. C., Teubner, J. K., Ryall, R. L. (1984) *Clin.Chem.* 30, 1339–1343.
23. Laker, M. F., Hofmann, A. F., Meeuse, B. J. (1980) *Clin.Chem.* 26, 827–830.
24. Potezny, N., Bais, R. O'Loughlin, P. D., Edwards, J. B., Rofe, A. M., Conyers, R. A. (1983) *Clin.Chem.* 29, 16–20.
25. Robertson, W. G. Urinary tract calculi. In: Metabolic bone and stone disease. B. E. C. Nordin, ed. Hong Kong, Churchill Livingston, pp. 271–326, 1984.
26. Khan, S. R. (1997) *World J. Urol.* 15, 236–243.

We claim:

1. A method for treating or preventing urinary stone disease comprising administering an effective amount of pyridoxamine to reduce urinary oxalate concentrations to an individual selected from the group consisting of an individual with urinary stone disease and an individual at risk for developing urinary stone disease.

2. The method of claim 1 wherein the method is for treating an individual with urinary stone disease.

3. The method of claim 2 wherein the urinary stone disease comprises the production of calcium oxalate urinary stones.

4. The method of claim 2 wherein the individual has hyperoxaluria.

5. The method of claim 4 wherein the hyperoxaluria comprises primary hyperoxaluria.

6. The method of claim 5 wherein the primary hyperoxaluria is Type I primary hyperoxaluria.

7. The method of claim 5 wherein the primary hyperoxaluria is Type II primary hyperoxaluria.

8. The method of claim 2 wherein the individual has hypercalciuria.

9. The method of claim 2 wherein the individual has hypocitraturia.

10. The method of claim 2 wherein the individual has idiopathic stone disease.

11. The method of claim 2 further comprising treating the individual with one or more compounds selected from the group consisting of (L)-2-oxothiazolidine-4-carboxylate (OTZ), allopurinol, inhibitors of aldehyde dehydrogenase, inhibitors of glycolate oxidase, nephrocalcin, and osteopontin.

12. The method of claim 2 further comprising treating the individual with one or more therapies selected from the group consisting of a reduced oxalate level diet and extracorporeal shock wave lithotripsy.

13. The method of claim 1 wherein the method is for preventing urinary stone disease, and wherein the individual is at risk for developing urinary stone disease.

14. The method of claim 13 wherein the individual has previously suffered from urinary stone disease.

15. The method of claim 13 wherein the individual has hyperoxaluria.

16. The method of claim 13 wherein the individual has a genetic defect predisposing the individual to primary hyperoxaluria.

17. The method of claim 16 wherein the defect predisposes the individual to Type I primary hyperoxaluria.

18. The method of claim 16 wherein the defect predisposes the individual to Type II primary hyperoxaluria.

19. The method of claim 13 wherein the individual has hypercalciuria.

20. The method of claim 13 wherein the individual has hypocitraturia.

21. The method of claim 13 further comprising treating the individual with one or more compounds selected from the group consisting of (L)-2-oxothiazolidine-4-carboxylate (OTZ), allopurinol, inhibitors of aldehyde dehydrogenase, inhibitors of glycolate oxidase, nephrocalcin, and osteopontin.

22. The method of claim 13 further comprising treating the individual with a reduced oxalate level diet.

* * * * *